(12) United States Patent
Graybill et al.

(10) Patent No.: US 10,376,358 B2
(45) Date of Patent: Aug. 13, 2019

(54) TEMPORARY DISPOSABLE SCAFFOLD STAND AND TOOLS TO FACILITATE RECONSTRUCTIVE VALVE SURGERY

(71) Applicant: Terumo Cardiovascular Systems Corporation, Ann Arbor, MI (US)

(72) Inventors: Matthew W. Graybill, Whitmore Lake, MI (US); Randal J. Kadykowski, South Lyon, MI (US); Kevin R. Line, Ann Arbor, MI (US)

(73) Assignee: TERUMO CARDIOVASCULAR SYSTEMS CORPORATION, Ann Arbor, MI (US)

( * ) Notice: Subject to any disclaimer, the term of this patent is extended or adjusted under 35 U.S.C. 154(b) by 61 days.

(21) Appl. No.: 15/594,080

(22) Filed: May 12, 2017

(65) Prior Publication Data

US 2017/0325940 A1    Nov. 16, 2017

Related U.S. Application Data

(60) Provisional application No. 62/335,729, filed on May 13, 2016.

(51) Int. Cl.
*A61F 2/24* (2006.01)
*B26F 1/40* (2006.01)

(52) U.S. Cl.
CPC .......... *A61F 2/2409* (2013.01); *A61F 2/2412* (2013.01); *A61F 2/2415* (2013.01); *A61F 2/2427* (2013.01); *B26F 1/40* (2013.01)

(58) Field of Classification Search
CPC ..... A61F 2/2415; A61B 17/32; A61B 17/322; Y10S 83/953; Y10S 83/954

USPC .............................. 600/36; 623/901; 83/701
See application file for complete search history.

(56) References Cited

U.S. PATENT DOCUMENTS

| 3,532,016 | A | * | 10/1970 | Lane | ...................... A61B 17/32 623/2.11 |
|---|---|---|---|---|---|
| 5,425,741 | A | * | 6/1995 | Lemp | ...................... A61B 17/32 606/167 |
| 5,609,600 | A | * | 3/1997 | Love | ...................... A61B 17/32 606/167 |
| 6,245,105 | B1 | | 6/2001 | Nguyen et al. | |
| 6,491,511 | B1 | | 12/2002 | Duran et al. | |
| 8,511,244 | B2 | | 8/2013 | Holecek et al. | |
| 9,044,246 | B2 | | 6/2015 | Goldfarb et al. | |
| 9,414,920 | B2 | | 8/2016 | Ozaki | |

(Continued)

*Primary Examiner* — Samuel G Gilbert
(74) *Attorney, Agent, or Firm* — Darryl Newell; MacMillan, Sobanski & Todd, LLC

(57) ABSTRACT

A device for joining individual leaflets for repairing a cardiac valve of a patient has a base and projection fingers rising from the base to support adjacent leaflets for tacking together by sewing overlapping edges of adjacent leaflets prior to emplacement into the patient. The invention provides a cutting tool for excising leaflets from a pericardial tissue sheet according to predetermined sizes and shapes. A leaflet having a desired contour and size is obtained by pressing the tool formed as a cutter block against the tissue sheet. A set of blocks can be provided wherein each cutter block has an outer edge following a respective contour and size for a leaflet, and wherein the outer edge includes a raised cutting edge for pressing through the pericardial tissue sheet. The blocks can be held in a press for assisting in pushing the cutting edge through the tissue.

3 Claims, 11 Drawing Sheets

(56) References Cited

U.S. PATENT DOCUMENTS

2010/0018447 A1\* 1/2010 Holecek ................ A61F 2/2415
112/217.1
2011/0000073 A1 1/2011 O'Fallon et al.
2015/0157456 A1 6/2015 Armstrong \* cited by examiner

TEMPORARY DISPOSABLE SCAFFOLD STAND AND TOOLS TO FACILITATE RECONSTRUCTIVE VALVE SURGERY

CROSS REFERENCE TO RELATED APPLICATIONS

This application claims the benefit of U.S. Provisional Application Ser. No. 62/335,729, filed May 13, 2016, which is incorporated herein by reference.

STATEMENT REGARDING FEDERALLY SPONSORED RESEARCH

Not Applicable.

BACKGROUND OF THE INVENTION

The present invention relates to a disposable temporary scaffold/holding fixture to facilitate assembly and implantation of valve leaflets. This benefits a surgeon by providing a structure to help aid in the use of tissue engineered material, allograft, xenograft, and autograft procedures.

There are currently available bio-prosthetic, biological, and mechanical aortic heart valves for human use. The steps involved with one typical procedure for fabrication of a total biological valve reconstruction involves the following:

1. The aorta is surgically dissected within open chest;
2. Calcified aortic valve leaflets are removed from the patient;
3. Commissure-to-commissure distances of the dissected aorta are sized with gages to determine what size individual leaflets will be required for reconstruction;
4. The gages are used to select corresponding tracing templates;
5. Individual valve leaflets are traced on biological tissue like the autologous pericardium;
6. Leaflets are cut and removed from tissue sheets; and
7. A surgeon carefully stitches each leaflet to the wall of the aorta.

This is a tedious manual procedure and it is time consuming. Various mediums (e.g., source materials) can be utilized for this application and are not limited to those in this example. It would be very desirable to reduce surgery time and the tedious assembly steps involved with individual leaflet installation.

SUMMARY OF THE INVENTION

To help reconstruct/fabricate and surgically implant valve leaflets, a temporary disposable scaffold/fixture is provided. In a preferred embodiment, an injected molded polymer based material forms a three dimensional scaffold to help hold individual leaflets in place for pre-assembly (i.e., stitching the leaflets together in a desired configuration). The device can also utilize various metals involving wire and/or tubing. The device can utilize a vacuum system to help hold the leaflets when a tube construction was used (similar to currently available heart stabilization suction devices).

The invention provides the surgeon with a tool to help hold leaflets as well as a simplified process. Once the leaflets are stitched in place, the scaffold is released from the leaflets and removed from the patient.

Thus, in one aspect of the invention, a device for joining individual leaflets for forming/reconstructing a valve or a portion of a valve in a cardiovascular system of a patient may comprises a base and projection fingers rising from the base to support adjacent leaflets for tacking together by sewing overlapping edges of the adjacent leaflets prior to emplacement into the cardiovascular system of a patient.

The invention further provides a cutting tool for excising leaflets from a pericardial tissue sheet, wherein a leaflet having a desired contour and size is obtained by pressing the tool against the sheet. A set of plates can be provided wherein each plate member has an outer edge following a respective contour and size for a leaflet, and wherein the outer edge includes a raised cutting edge for pressing through the pericardial tissue sheet.

DETAILED DESCRIPTION OF PREFERRED EMBODIMENTS

Figure 1:
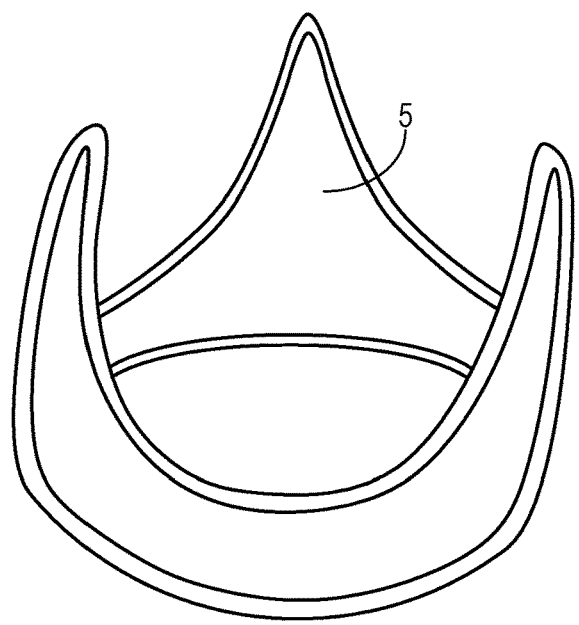
FIG. 1 is a perspective view of a scaffold of the present invention.
Figure 2:
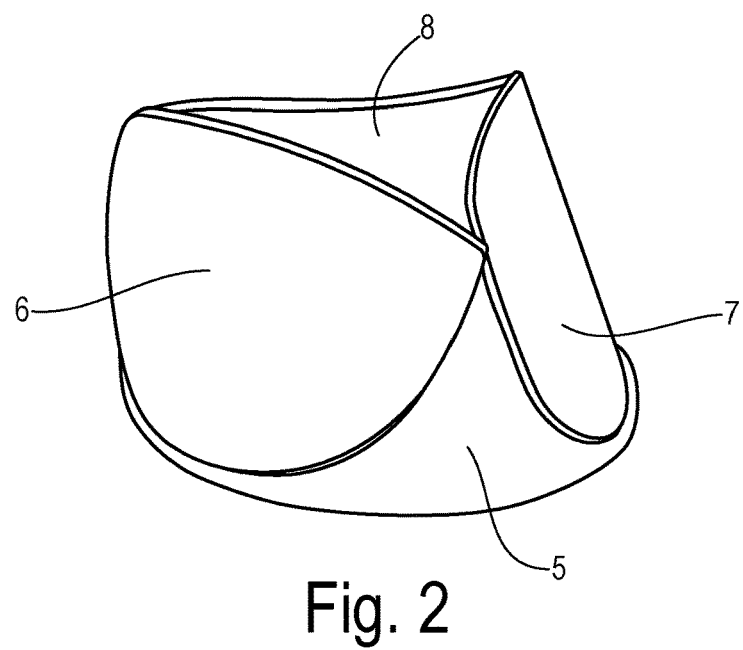
FIG. 2 is a perspective view of leaflets suspended on a scaffold.

Referring to FIG. 1, a scaffold 5 has three fingers extending upwardly from a generally circular base. Scaffold 5 can be a polymer molded structure, stainless steel wireframe, or a tubing structure (either metal or plastic tubing). Sections of scaffold 5 could be detachable and/or adjustable. It could be made to be disposable or re-usable. The upwardly extending fingers correspond to the locations between adjacent leaflets for reconstructing a valve. As shown in FIG. 2, previously prepared individual leaflets 6, 7, and 8 can be placed onto scaffold 5 for stitching together at adjacent edges in preparation for insertion into a patient.

Figure 3:
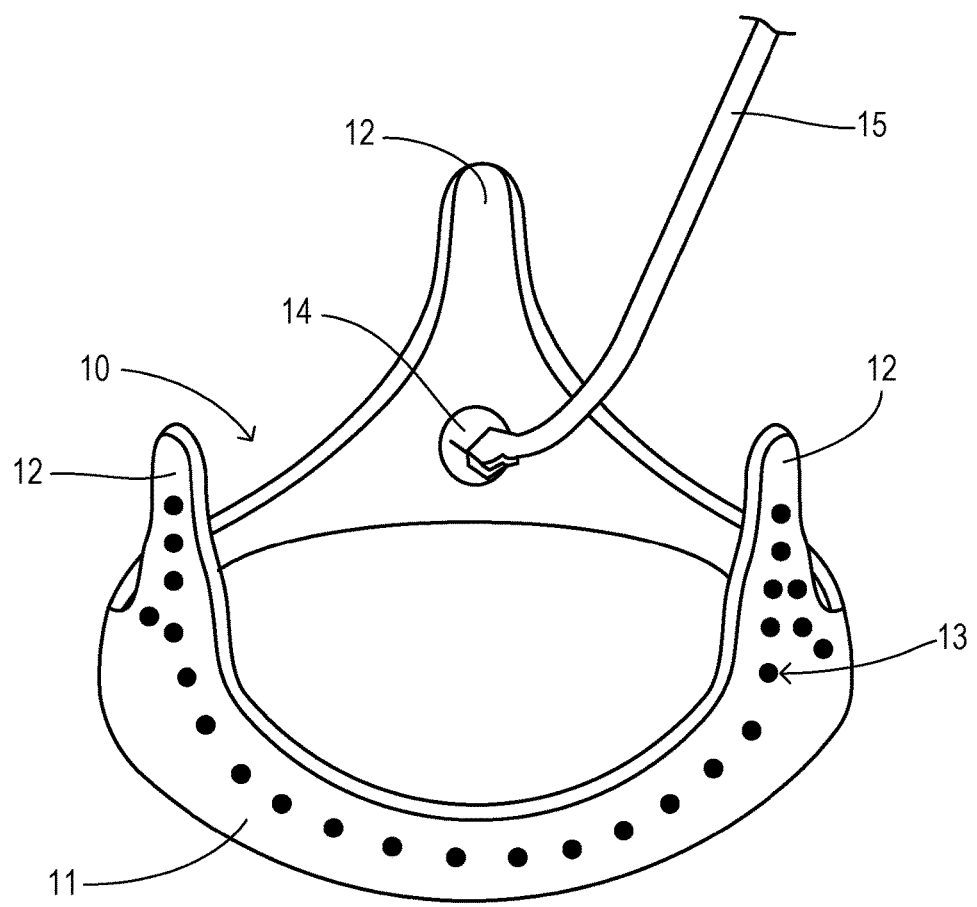
FIG. 3 is a perspective view of another embodiment of a scaffold having suction.
Figure 4:
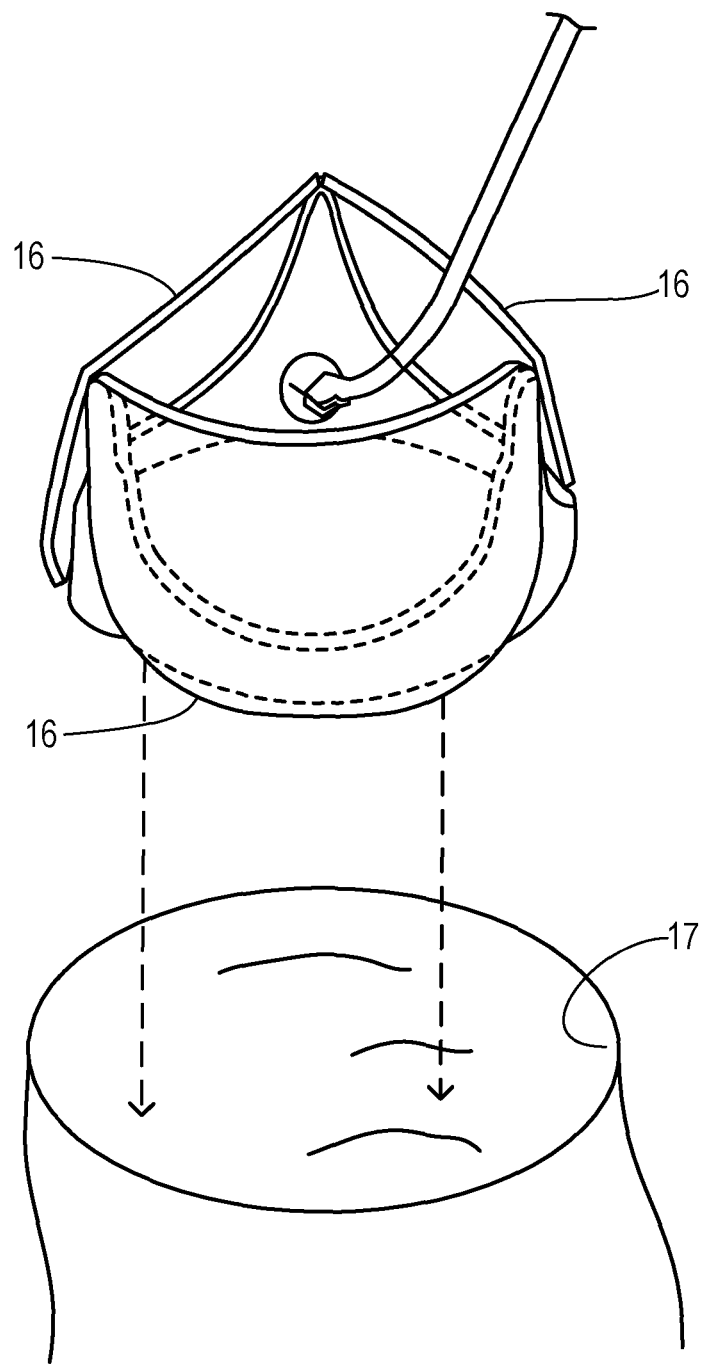
FIG. 4 is a perspective view of pre-stitched leaflets suspended on a scaffold being inserted into an aorta.

As shown in FIG. 3, another embodiment of a scaffold 10 includes a circular base 11 supporting upward projections 12 spaced by about 120° and corresponding to the commissures to be made between adjacent leaflets. Scaffold 10 is comprised of a hollow body with an inner chamber communicating with a plurality of suction holes 13 disposed along the edges of base 11 and projections 12. A vacuum may be introduced via a conduit 15 connected to a port 14 on scaffold 10 to draw a gentle vacuum at holes 13 to gently retain leaflets that have been pre-cut to an appropriate size. As shown in FIG. 4, leaflets 16 are draped onto the outer periphery of scaffold 10 to be held in place by vacuum pressure. The edges of adjacent leaflets can also be tacked together with a suture if desired. With the leaflets held in place, scaffold 10 is lowered into an aorta 17 that has been prepared for having the leaflets attached in a configuration to function as an aortic valve as known in the art.

Figure 5:
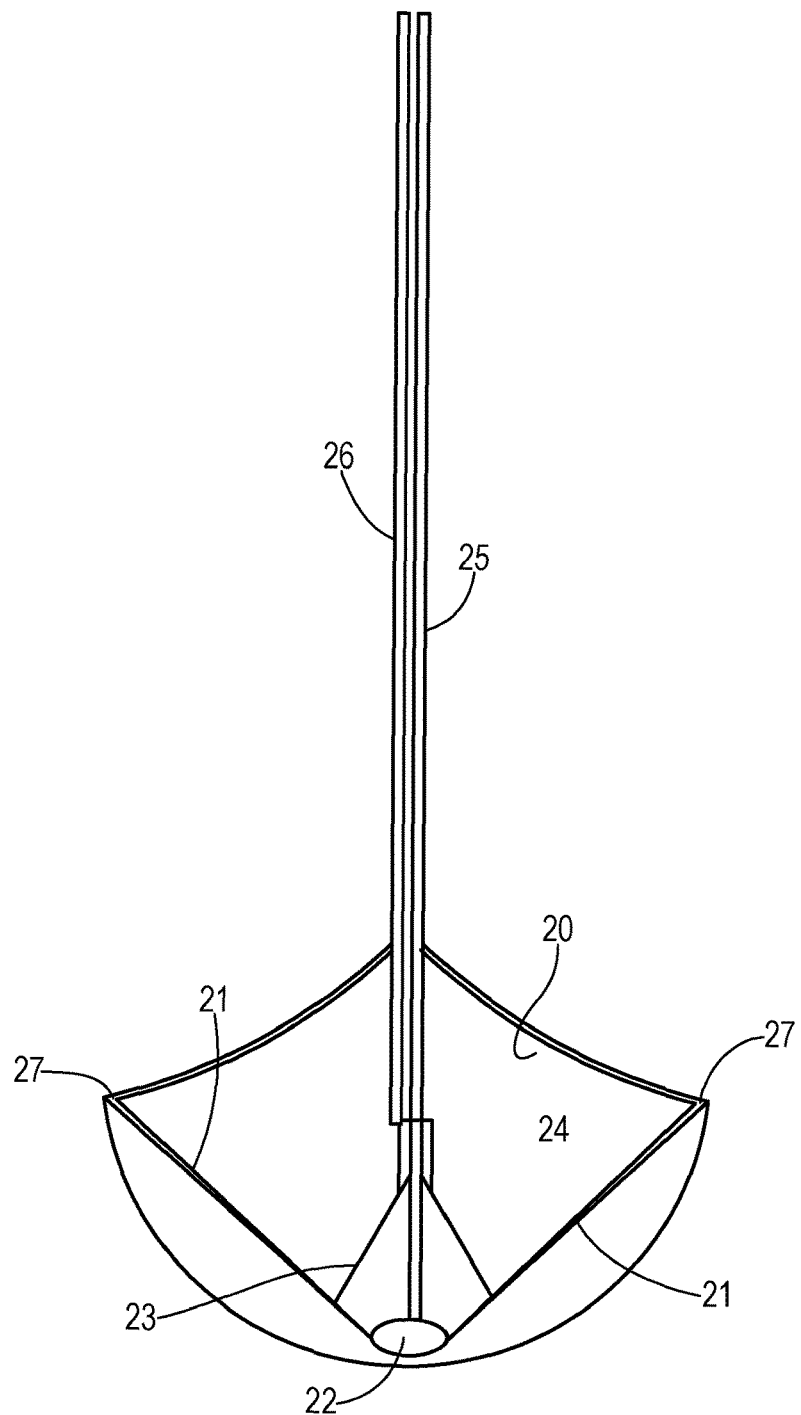
FIG. 5 is a side view of an umbrella spreader for holding open an aorta.

The device shown in FIG. 5 represents an umbrella type holder that can also hold a leaflet and place it into position for stitching it into the aorta. The frame of the umbrella has attachment points to gently hold the leaflet. Another feature of this design may be to have a tubular frame that can have a suction line attached via a handle. The suction may allow the leaflet to be held with slight vacuum pressure to aid in assembly.

More specifically, umbrella holder preferably includes a flexible fabric canopy 20 supported by articulating umbrella arms 21 and joined to an end piece 22. Control arms 23 are connected between arms 21 and a slider 24 that slides on a fixed rod 25 under control of a sliding rod 26. There are three arms 21 separated by about 120°, each arm 21 ending in an attachment point 27 for temporarily attaching respective leaflets either by suction holes at the attachment points or by a mechanical attachment such as a suture. Canopy 20 is expanded for supporting the leaflets during initial placement into the aorta. After suturing, canopy 20 may be collapsed and the holder removed. In addition, the umbrella holder could be configured to perform testing of the valve after suturing. To do so, the free ends of the leaflets could be temporarily attached to canopy 20 between attachment points 27 so that canopy 20 could be moved between its expanded and collapsed positions to determine whether the leaflets have achieved the desired range of motion.

Figure 6:
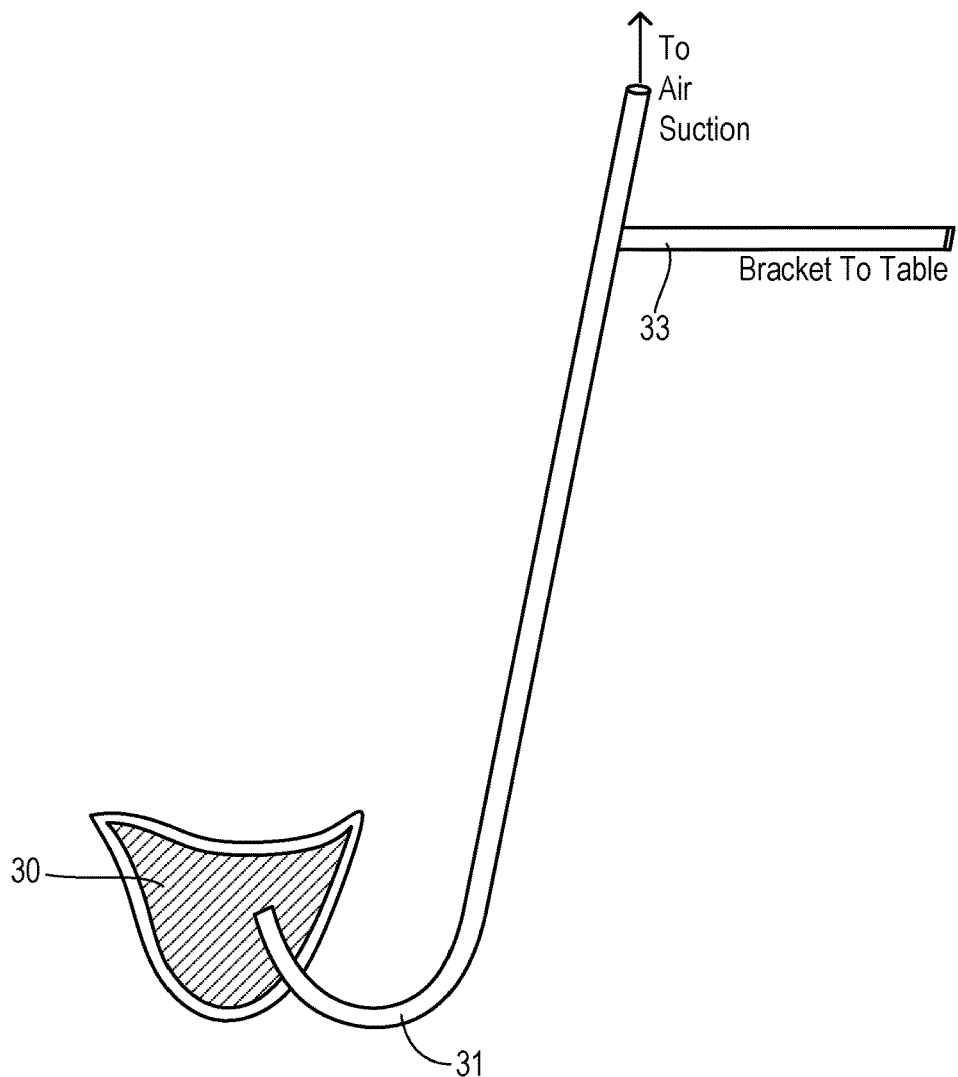
FIG. 6 is a perspective view of a leaflet holder of the invention.
Figure 7:
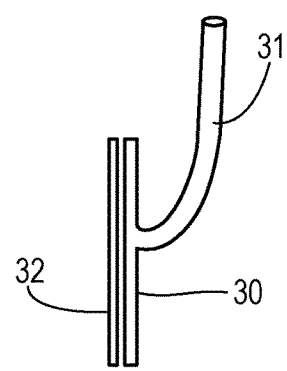
FIG. 7 is a side view of the holder of FIG. 6.
Figure 8:
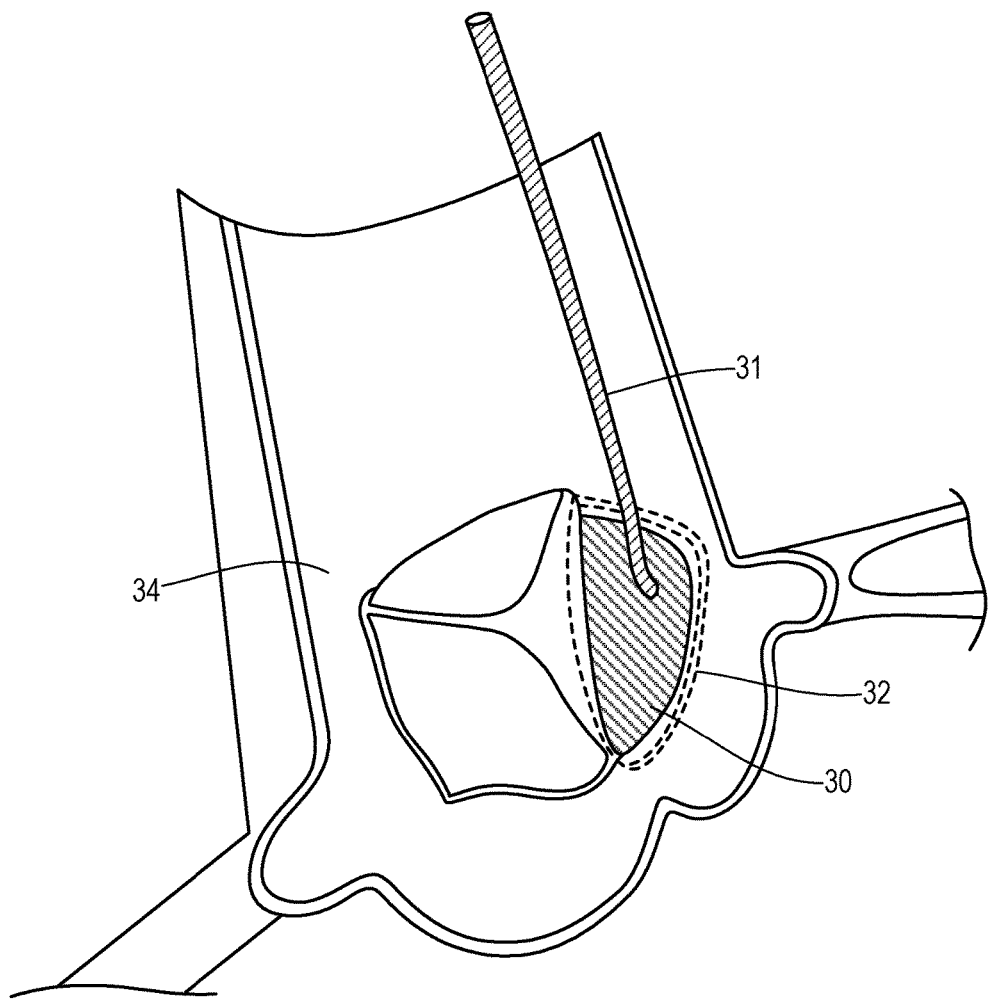
FIG. 8 is a perspective view of a leaflet being held in position within an aorta by the holder of FIG. 6.

The device shown in FIGS. 6-8 comprises a plastic or stainless steel tissue holder and handle that can mount to a retractor (not shown). This affords the user a hands free holding tool. The surface of the leaflet holder is vacuum actuated to help hold leaflets in place. The tubular wall has small holes along the perimeter and some on the surface to hold the leaflet. The surgeon or assistant can position the leaflet and then remove suction and proceed to the next leaflet.

Referring to FIGS. 6 and 7, the holder is comprised of a hollow paddle 30 including suction holes in an exposed leaflet-receiving surface on one side and a vacuum port on the other side which is connected to a suction line 31. Suction line 31 is preferably a rigid tube which may be mechanically connected to a support arm or bracket 33 that can be locked in place after adjusting the position of leaflet 32 carried by paddle 30 to the desired position for suturing, thereby providing hands-free support for ease of suturing. FIG. 8 shows leaflet 32 being held in place within an aorta 34 undergoing valve replacement.

Figure 9:
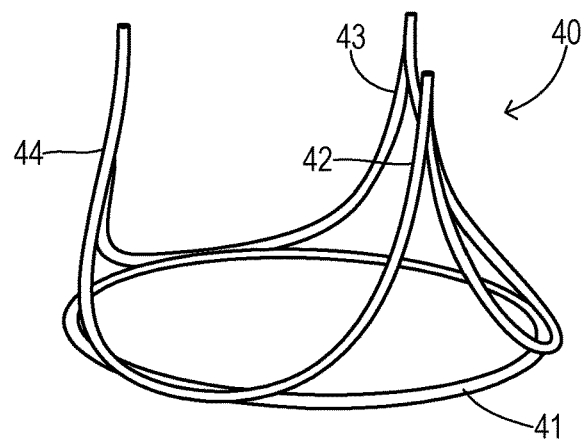
FIG. 9 is a perspective view of another embodiment of a scaffold of the invention.
Figure 10:
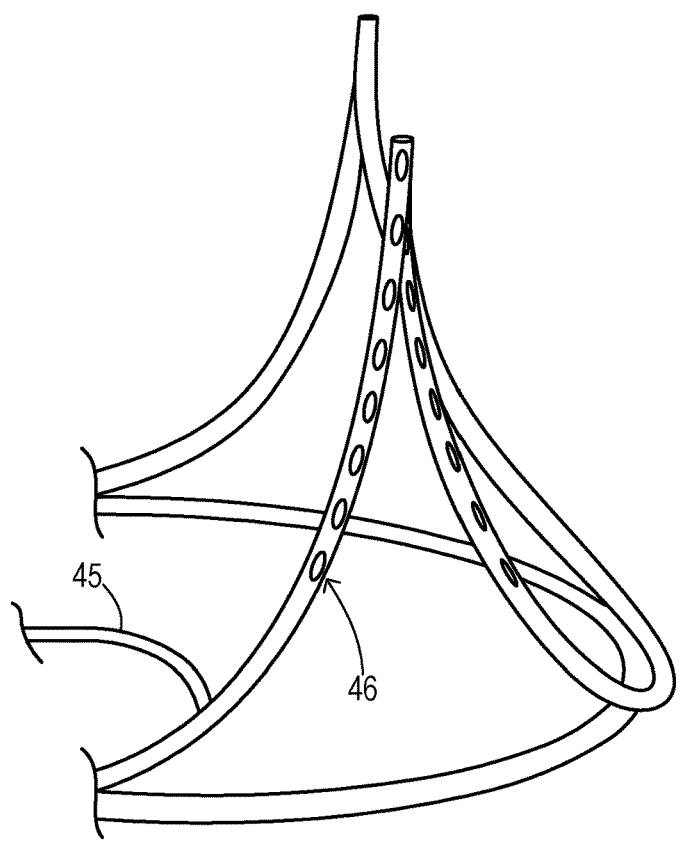
FIG. 10 is a detail view of the scaffold of FIG. 9 showing suction holes.

FIG. 9 shows a scaffold 40 comprised of thin tubing which can be made from biocompatible metal, for example. A base ring 41 allows scaffold 40 to be free-standing on a convenient surface outside the patient to allow a surgeon to sew together the corners of adjacent leaflets to form a 3D valve which can later be transferred into the patient for implantation. Projections 42, 43, and 44 provide a frame that is arranged to hold three adjacent leaflets (not shown) which have been created (e.g., cut from pericardial tissue) with appropriate overlaps as held in place using suction applied via a suction tube 45 to suction holes 46 as shown in FIG. 10.

Figure 11:
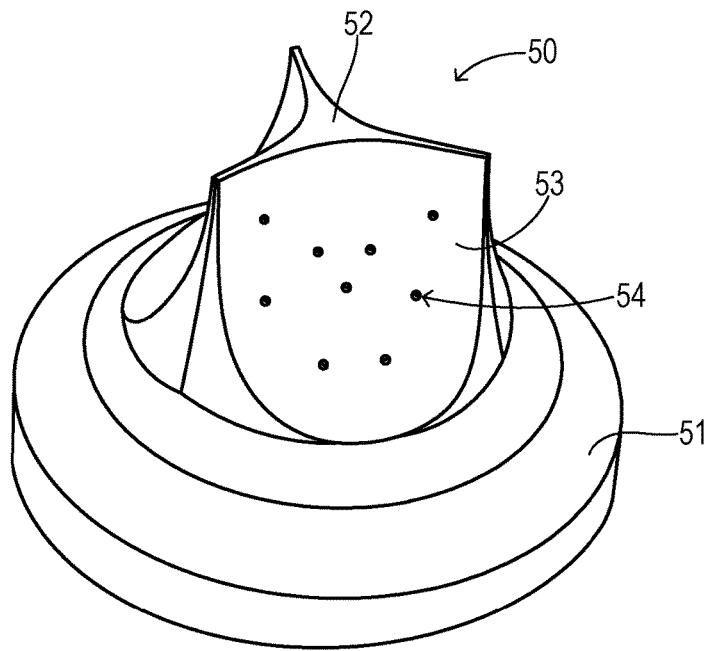
FIG. 11 is a perspective view of another embodiment of a suction frame for pre-suturing two or more leaflets.

FIG. 11 shows another embodiment of a self-standing scaffold 50 having a base section 51 and a frame section 52, wherein scaffold 50 is formed as a plastic-molded hollow body. Base section 51 is adapted to be connected to a vacuum source (not shown), whereby suction pressure is drawn at a plurality of suction holes 54 on a concave leaflet-holding surface 53, for example.

Figure 12:
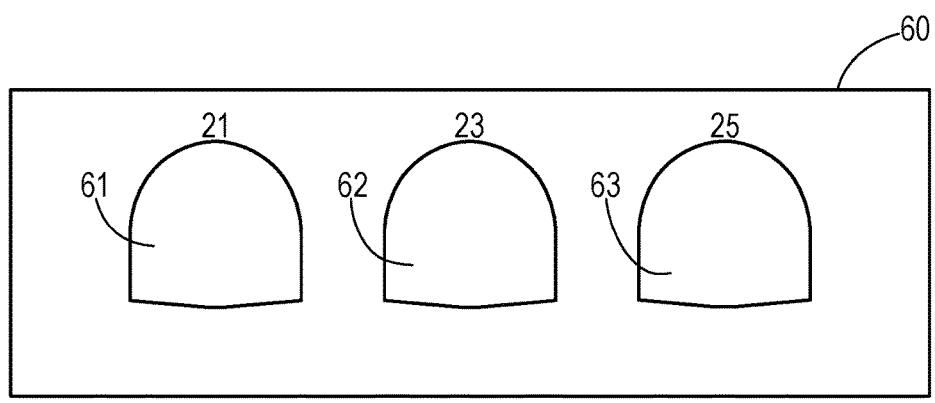
FIG. 12 is a plan view of a prior art template for marking a tissue sheet as a stencil for cutting a leaflet using scissors.

Regarding the formation of leaflets for use on the scaffolds, thin tissue sheet(s) may be excised from the pericardium tissue having a desired thickness. Then, a desired shape for each leaflet is cut, usually with the help of a template of a chosen size. FIG. 12 shows a typical prior art stencil which acts as a template for cutting a desired leaflet from a tissue sheet. A plate 60 has a plurality of patterned openings 61-63 with respective sizes and/or shapes of the type useful for valve reconstruction. A desired pattern is traced onto the tissue (e.g., with a biocompatible marking pen) and then cut out using scissors.

Figure 13:
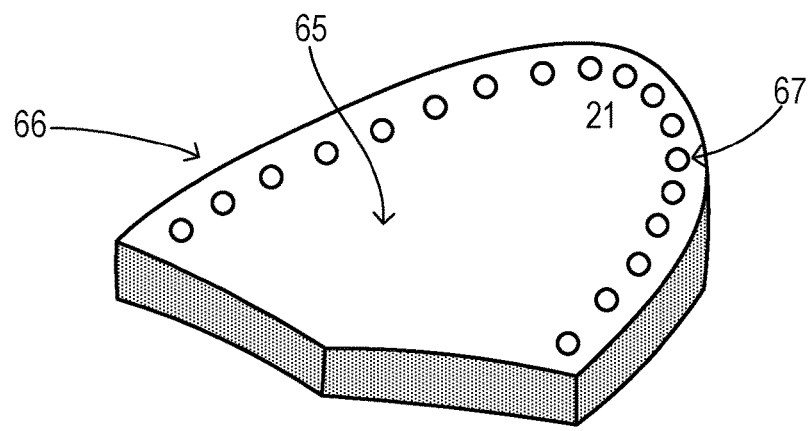
FIG. 13 is a perspective view of a sized cutter block of the invention.

Leaflet formation can be improved by the present invention through the use of a "cookie cutter" approach in which the sharp edge(s) of a cutter circumscribe the desired shape and penetrate the tissue in one pressing motion. For example, an "individual cutter" 65 as shown in FIG. 13. Cutter 65 is comprised of a plate member having the desired contour and size for a particular leaflet. Thus, a plurality of such cutters would be provided in a kit having a variety of different sizes and/or contours to allow a surgeon to create leaflets matched to a particular patient.

Individual cutter 65 has a sharp outer cutting edge 66 that may be pressed into a tissue sheet to remove a leaflet with a desired contour/size. Cutter 65 may further include a plurality of raised posts 67 to create depressions along the suturing edges of a leaflet as a guide for suturing. The depressions preferably would not puncture the tissue but would be sufficiently visible to be discerned by the surgeon.

Figure 14:
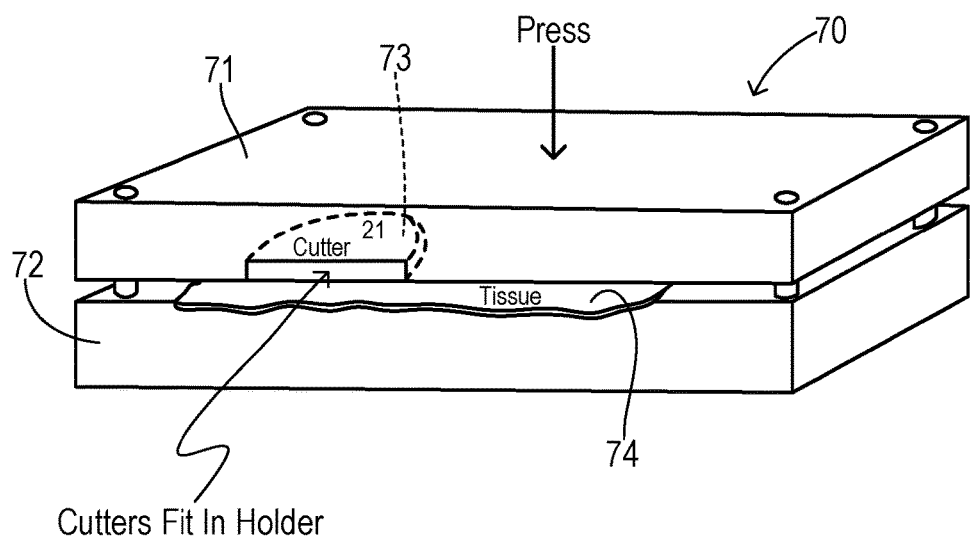
FIG. 14 is a perspective view of a cutter press using block according to FIG. 13 to cut appropriately sized leaflets without marking by a template.

Individual cutter 65 can be used alone or with a fixture, such as a press 70 shown in FIG. 14. Press 70 has an upper plate 71 and a lower plate 72, wherein an individual cutter can be removably inserted into a socket in a lower surface of upper plate 71 so that a cutting edge and raised posts of a selected cutter are presented to a tissue sheet 74 that rests on an upper surface of lower plate 72. By pressing plates 71 and 72 together, tissue sheet 74 is cut so that a desired leaflet is obtained.

Figure 15:
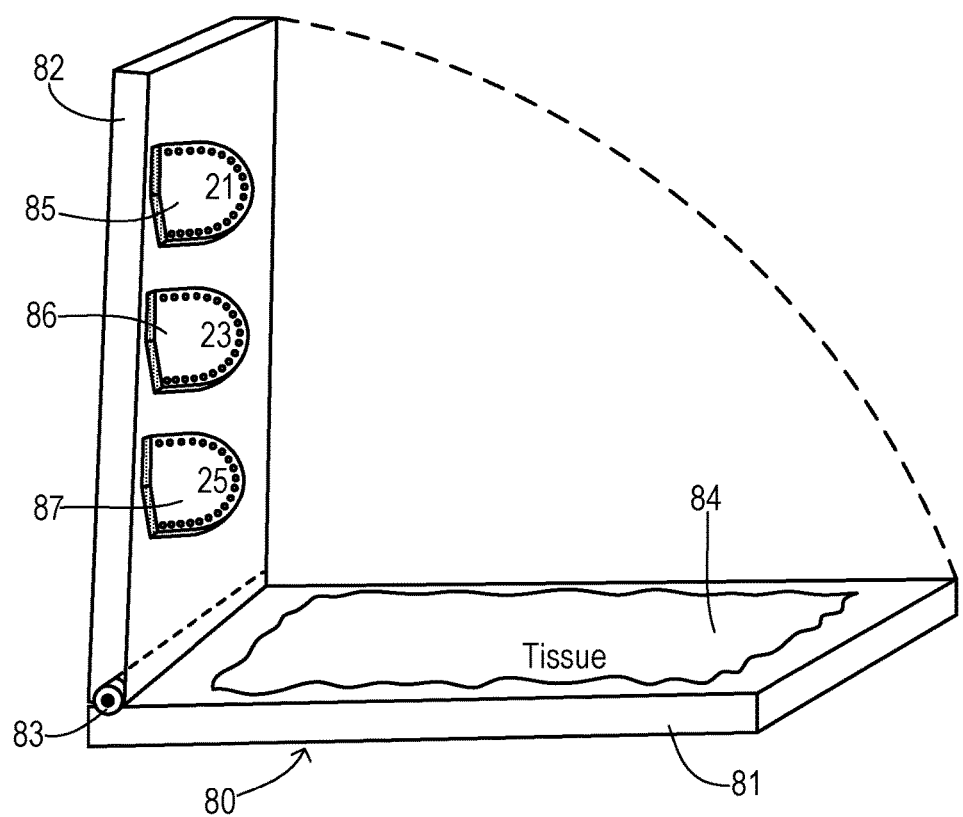
FIG. 15 is a perspective view showing another embodiment for a press receiving selected cutter blocks.

FIG. 15 shows another embodiment of a press 80 wherein a lower plate 81 and an upper plate 82 are joined by a hinge 83. Lower plate 81 has a shallow bowl 84 for retaining a tissue sheet. Upper plate 82 has a plurality of sockets each holding a respective cutter 85, 86, and 87 for simultaneously cutting out respective leaflets.

Figure 16:
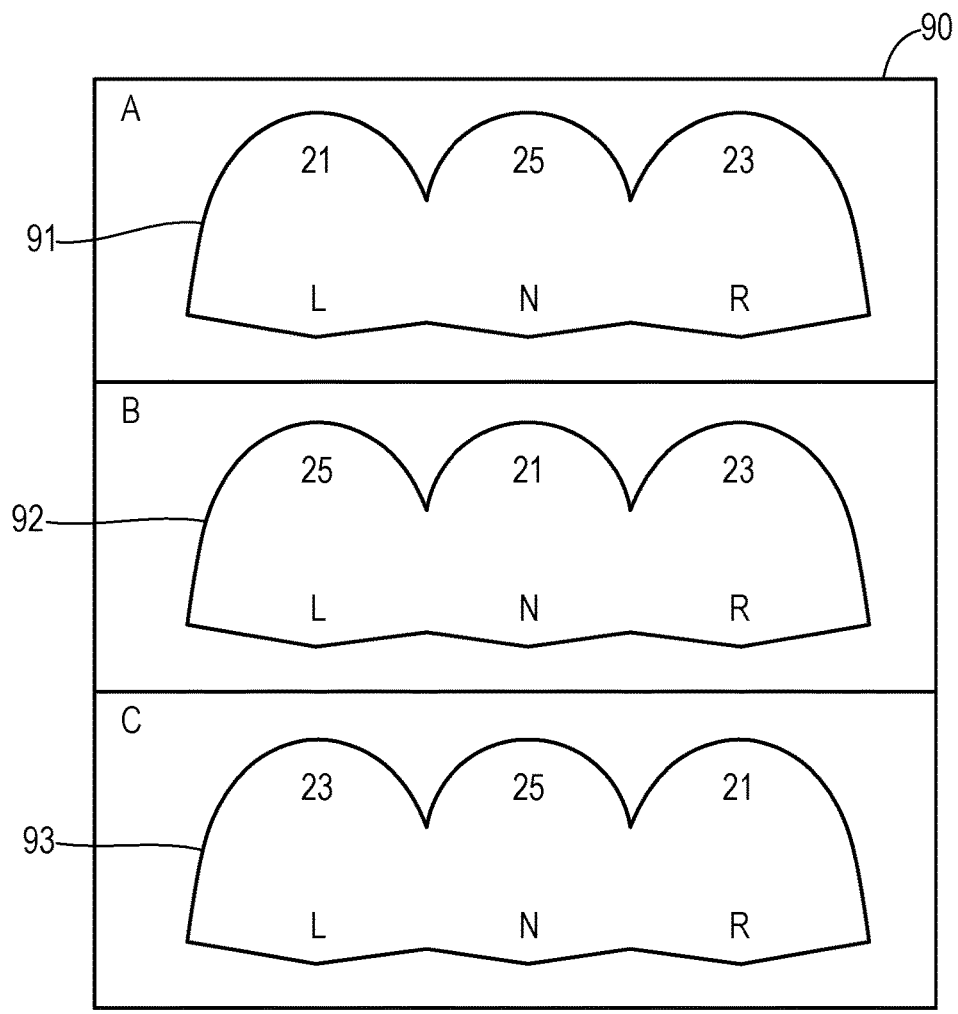
FIG. 16 is a plan view showing a set of cutter blocks wherein each block can simultaneously cut a plurality of leaflets as one unit.

Leaflets may be cut individually as shown in FIGS. 13-15, or they can be cut as a single continuous piece of tissue as shown in FIG. 16. By forming as a single piece, less sewing would be required since the commissures between adjacent leaflets would already be partially joined. In order to form unified sets of leaflets, corresponding templates or cutters are constructed with the capacity to cut a tissue sheet according to the desired patterns. FIG. 16 shows a first pattern A for creating a unified leaflet set with particular leaflet sizes at particular positions in the set. A plate 90 may have a raised structure 91 with a protruding cutting edge defining the outer boundary of the leaflet set (and may also include raised posts to create sewing guide depressions). Alternatively, 91 may instead indicate an aperture within plate 90 for use as a stencil to cut a unified leaflet from a tissue sheet using a separate knife, for example. Patterns B and C show additional structures 92 and 93 that may be included in a kit that allows a surgeon to select a cutting block that provides the desired size and arrangement of leaflets needed to match the anatomy of a particular patient.

What is claimed is:

1. A cutting device for cutting a leaflet from a pericardial tissue sheet, comprising:
   a set of plate members having a plurality of predetermined leaflet contours and sizes adapted to allow selection of a respective one of the plate members from the set of plate members to match an anatomy of a patient; and
   a raised cutting edge projecting from each of the plate members of the set of plate members configured to cut a leaflet according to the predetermined contour and size of each of the respective plate members in response to pressing against the pericardial tissue sheet;
   wherein each of the respective plate members further includes raised posts for forming sewing depressions into the pericardial tissue sheet to guide sewing of the leaflet.

2. The cutting device of claim 1 wherein each raised cutting edge of a respective plate member of the set of plate members follows a contour and size for a plurality of unified leaflets for pressing against the pericardial tissue sheet to create an integral leaflet set.

3. The cutting device of claim 1 further comprising:
   a press having upper and lower press plates, wherein the upper press plate is adapted to removably retain a selected plate member of the set of plate members as a cutter block for a desired leaflet contour and size, and wherein the lower press plate is adapted to support the pericardial tissue sheet and provides a reaction surface to allow the raised cutting edge of the selected plate member to penetrate the pericardial tissue sheet.

* * * * *